(12) United States Patent
Wang

(10) Patent No.: US 12,232,709 B2
(45) Date of Patent: Feb. 25, 2025

(54) BIOPSY NEEDLE AND PUNCTURE BIOPSY DEVICE

(71) Applicant: SUZHOU LEAPMED HEALTHCARE CORPORATION, Suzhou (CN)

(72) Inventor: Qin Wang, Suzhou (CN)

(73) Assignee: SUZHOU LEAPMED HEALTHCARE CORPORATION, Suzhou (CN)

( * ) Notice: Subject to any disclaimer, the term of this patent is extended or adjusted under 35 U.S.C. 154(b) by 877 days.

(21) Appl. No.: 17/422,745

(22) PCT Filed: Jan. 14, 2019

(86) PCT No.: PCT/CN2019/071544
§ 371 (c)(1),
(2) Date: Jul. 14, 2021

(87) PCT Pub. No.: WO2020/146968
PCT Pub. Date: Jul. 23, 2020

(65) Prior Publication Data
US 2022/0087656 A1    Mar. 24, 2022

(51) Int. Cl.
*A61B 10/02*    (2006.01)

(52) U.S. Cl.
CPC .. *A61B 10/0233* (2013.01); *A61B 2010/0208* (2013.01)

(58) Field of Classification Search
CPC ........ A61B 10/0233; A61B 2010/0208; A61B 10/0275; A61B 2017/0046
See application file for complete search history.

(56) References Cited

U.S. PATENT DOCUMENTS

| | | | |
|---|---|---|---|
| 2013/0041256 A1* | 2/2013 | Fiebig | A61B 17/3468 600/432 |
| 2019/0117201 A1* | 4/2019 | Beck | A61B 10/025 |

\* cited by examiner

*Primary Examiner* — Andrey Shostak
(74) *Attorney, Agent, or Firm* — Swidler Law Group, LLC; Sean S. Swidler

(57) ABSTRACT

The present invention provides a biopsy needle and a puncture biopsy apparatus. The biopsy needle includes: an inner needle assembly, including a first plug-in portion plugged in with a fastener; an outer needle assembly, including a second plug-in portion plugged in with the fastener; and the fastener, including a third plug-in portion plugged in with the first plug-in portion, and a fourth plug-in portion plugged in with the second plug-in portion. According to the biopsy needle and the puncture biopsy apparatus provided in the present invention, the biopsy needle can be assembled and disassembled in a simple and fast way, helping reduce preparation time and preparation work for a surgery, thereby improving surgery efficiency.

16 Claims, 3 Drawing Sheets

BIOPSY NEEDLE AND PUNCTURE BIOPSY DEVICE

TECHNICAL FIELD

The present invention relates to the technical field of medical apparatuses, and in particular, to a biopsy needle and a puncture biopsy apparatus.

BACKGROUND

Bone and soft tissue tumors are diseases seriously endangering human health and life. In recent years, the respective incidence rates have gradually increased, and ages of onset those incidence have gradually decreased. Early detection, correct diagnosis, and timely treatment play an important role in prognosis. Correct diagnosis requires a combination of clinic, imaging, and pathology, among which pathological diagnosis plays a key role in choosing treatment options. Needle biopsy is a main approach to obtain pathological diagnosis.

In a needle biopsy surgery, a surgical operator determines a location of a to-be-sampled by using a device such as an imaging machine, and then performs a needle biopsy operation. Before the biopsy surgery, a preparation person takes out a biopsy needle and loads it onto a biopsy gun. The surgical operator uses the prepared biopsy gun to perform a biopsy sampling operation on a patient, with the assistance of the imaging device. However, current biopsy guns have some problems in use. According to an existing biopsy gun operation method, after a biopsy needle is loaded onto a biopsy gun, a part of the biopsy needle is forcefully squeezed open and then pulled out, and then a top cover is put on the biopsy gun. Many operations are required for assembling the biopsy needle. Therefore, loading the biopsy needles available on the market onto the biopsy guns is time-consuming and also difficult.

SUMMARY

In view of this, the present invention provides a biopsy needle and a puncture biopsy apparatus. The biopsy needle can be assembled and disassembled in a simple and fast way, thereby reducing preparation time for a surgery.

To achieve the foregoing objectives, according to an aspect of the present invention, a biopsy needle is provided.

The biopsy needle in the present invention includes: an inner needle assembly, including a first plug-in portion plugged in with a fastener, where the first plug-in portion includes two first outer limiting walls arranged in parallel and a first limiting plate located between the two first outer limiting walls, and the first limiting plate is provided with a first protrusion; an outer needle assembly, including a second plug-in portion plugged in with the fastener, where the second plug-in portion includes two second outer limiting walls arranged in parallel and a second limiting plate located between the two second outer limiting walls, and the second limiting plate is provided with a second protrusion; and the fastener, including a third plug-in portion plugged in with the first plug-in portion, and a fourth plug-in portion plugged in with the second plug-in portion, where the third plug-in portion includes two first inner limiting walls that have a T-shaped longitudinal section and that match the first outer limiting walls, and a third limiting plate arranged between the two first inner limiting walls and matching the first limiting plate, where the third limiting plate is provided with a first groove mating with the first protrusion; and the fourth plug-in portion includes two second inner limiting walls that have a T-shaped longitudinal section and that match the second outer limiting walls, and a fourth limiting plate arranged between the second inner limiting walls and matching the second limiting plate, where the fourth limiting plate is provided with a second groove mating with the second protrusion.

Optionally, the first outer limiting walls are arranged perpendicular to the first limiting plate, and a first gap is provided between each of the first outer limiting walls and the first limiting plate; two first sliding slots are symmetrically provided on a surface of the first limiting plate facing away from the first protrusion; the second outer limiting walls are arranged perpendicular to the second limiting plate, and a second gap is provided between each of the second outer limiting walls and the second limiting plate; and two second sliding slots are symmetrically provided on a surface of the second limiting plate facing away from the second protrusion.

Optionally, a third gap is provided between each of the first inner limiting walls and the third limiting plate; and when the fastener is connected to the inner needle assembly, the first inner limiting walls are inserted into the first gaps, the first limiting plate is inserted into the third gaps, the first sliding slots abut against the top of the first inner limiting walls, and the first limiting plate abuts against the third limiting plate, so that the first protrusion mates with the first groove.

Optionally, a fourth gap is provided between each of the second inner limiting walls and the third limiting plate; and when the fastener is connected to the outer needle assembly, the second inner limiting walls are inserted into the second gaps, the second limiting plate is inserted into the fourth gaps, the second sliding slots abut against the top of the second inner limiting walls, and the second limiting plate abuts against the fourth limiting plate, so that the second protrusion mates with the second groove.

Optionally, the inner needle assembly is nested within the outer needle assembly, and the first plug-in portion protrudes from the outer needle assembly.

Optionally, the outer needle assembly further includes a hollow second needle body at one end of the second plug-in portion, the second needle body has an opening at each end, and the end of the second needle body is of a needle-like structure; the inner needle assembly further includes a first needle body at one end of the first plug-in portion, and the end of the first needle body is of a needle-like structure disposed in a direction opposite the needle-like structure at the end of the second needle body; and an accommodating portion is provided on the first needle body at a location close to the end of the first needle body.

Optionally, the first plug-in portion further includes a first connection portion connected to the first needle body, and a first hole; planes corresponding to the first limiting plate, the first connection portion, and the first hole are perpendicular to each other; and the biopsy needle is connected to a biopsy gun through the first hole.

Optionally, the second plug-in portion further includes a second connection portion connected to the second needle body, and a second hole, and planes corresponding to the second limiting plate, the second connection portion, and the second hole are perpendicular to each other; and the biopsy needle is connected to the biopsy gun through the second hole.

Optionally, the second plug-in portion further includes a third connection portion on a same axis as the second connection portion, the third connection portion runs through the second plug-in portion and the second needle body, and the first needle body enters the second plug-in portion through the third connection portion, and then enters the second needle body.

Optionally, the third plug-in portion and the fourth plug-in portion are on a same side of the fastener and arranged in parallel.

Optionally, the fastener further includes a pull portion and a through hole on one side of the pull portion.

According to another aspect of the present invention, a puncture biopsy apparatus is provided.

The puncture biopsy apparatus according to the present invention includes a biopsy gun and a biopsy needle.

According to the technical solutions of the present invention, the inner needle assembly and the fastener are plugged in together through the first protrusion of the first plug-in portion and the first groove of the third plug-in portion, and the outer needle assembly and the fastener are plugged in together through the second protrusion of the second plug-in portion and the second groove of the fourth plug-in portion. With this connection method, the assembly and disassembly operations are simple, eliminating the step of forcibly squeezing the biopsy needle open, and the assembly and disassembly time is short, helping reduce preparation time and preparation work for a surgery, thereby improving surgery efficiency. In addition, the biopsy needle in the present invention has a simple structure and therefore can reduce mold costs of the biopsy needle and time for an employee to assemble the biopsy needle, thereby reducing production costs for a company.

BRIEF DESCRIPTION OF DRAWINGS

The drawings are used for a better understanding of the present invention, and do not constitute improper limitation on the present invention.

Figure 1:
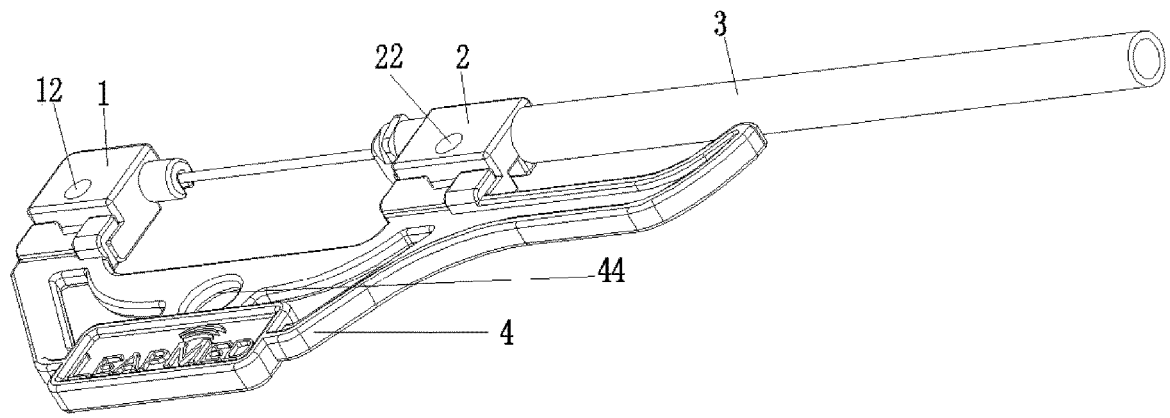
FIG. 1 is a schematic structural diagram of a biopsy needle according to an embodiment of the present invention.
Figure 2:
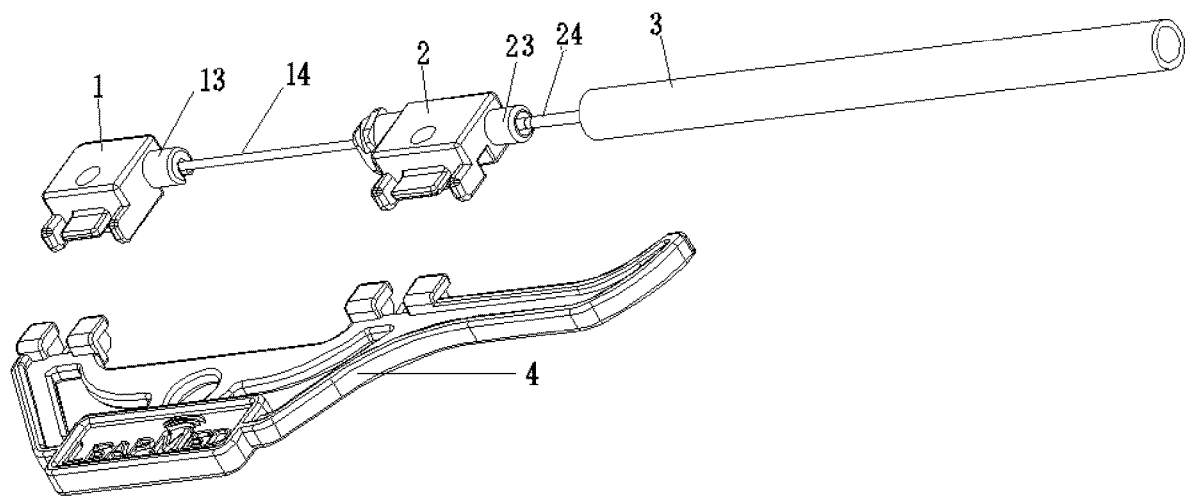
FIG. 2 is a schematic exploded view of a biopsy needle according to an embodiment of the present invention.
Figure 3:
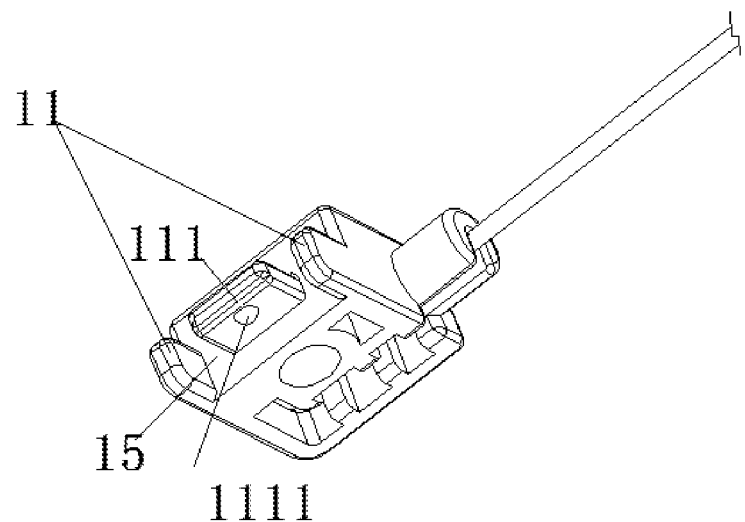
FIG. 3 is a schematic structural diagram of an inner needle assembly of a biopsy needle according to an embodiment of the present invention.
Figure 4:
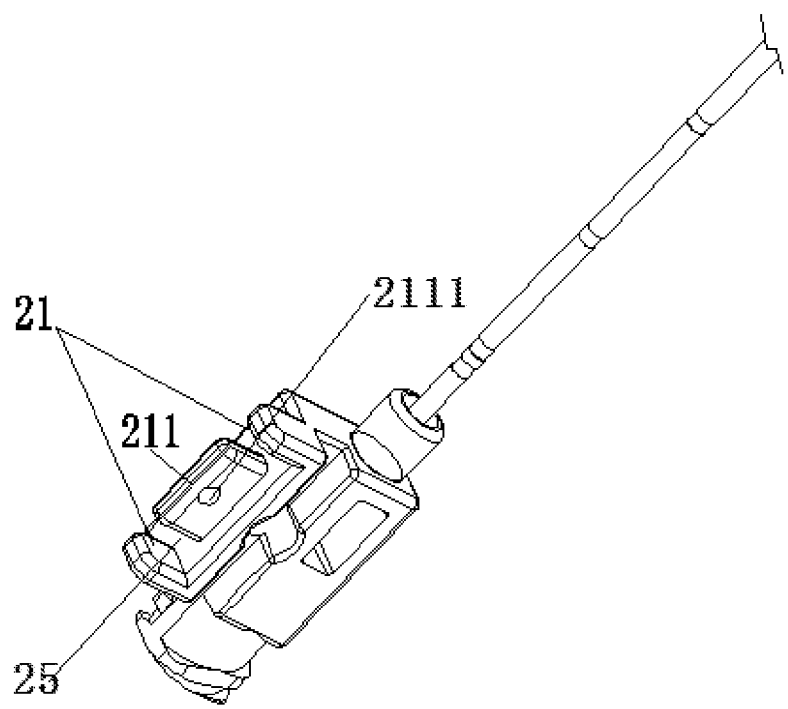
FIG. 4 is a schematic structural diagram of an outer needle assembly of a biopsy needle according to an embodiment of the present invention.
Figure 5:
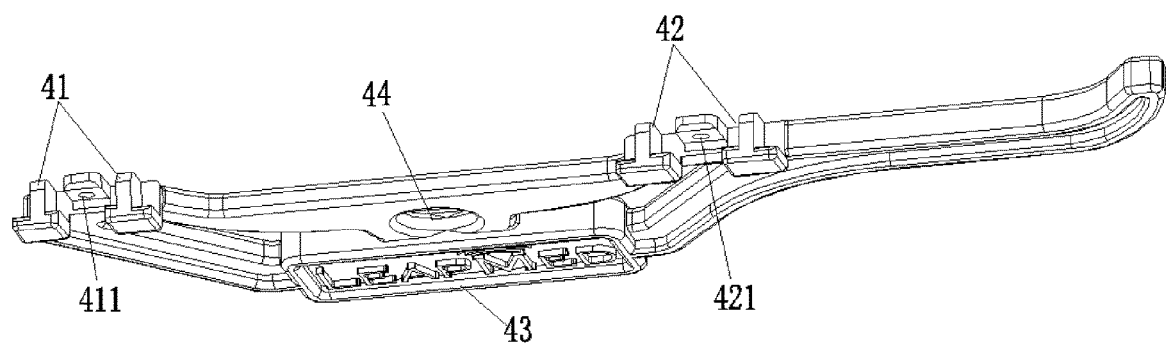
FIG. 5 is a schematic structural diagram of a fastener of a biopsy needle according to an embodiment of the present invention.

1. inner needle assembly; 11. first outer limiting wall; 111. first limiting plate; 1111. first protrusion; 12. first hole; 13. first connection portion; 14. first needle body; 15. first gap; 2. outer needle assembly; 21. second outer limiting wall; 211. second limiting plate; 2111. second protrusion; 22. second hole; 23. second connection portion; 24. second needle body; 25. second gap; 3. protective cover; 4. fastener; 41. first inner limiting wall; 411. first groove; 42. second inner limiting wall; 421. second groove; 43. pull portion; 44. through hole; 6. biopsy gun; and 61. cover.

DESCRIPTION OF EMBODIMENTS

The following describes example embodiments of the present invention with reference to the accompanying drawings, including various details of the embodiments of the present invention to facilitate understanding. Therefore, the description should be merely regarded as examples. Therefore, a person of ordinary skill in the art should understand that various changes and modifications can be made to the embodiments described herein without departing from the scope and spirit of the present invention. Likewise, for clarity and conciseness, descriptions of well-known functions and structures are omitted in the following description.

As shown in FIG. 1, FIG. 2, FIG. 3, FIG. 4, and FIG. 5, a biopsy needle in the present invention includes: an inner needle assembly 1, including a first plug-in portion plugged in with a fastener 4, where the first plug-in portion includes two first outer limiting walls 11 arranged in parallel and a first limiting plate 111 located between the two first outer limiting walls 11, and the first limiting plate 111 is provided with a first protrusion 1111;

an outer needle assembly 2, including a second plug-in portion plugged in with the fastener 4, where the second plug-in portion includes two second outer limiting walls 21 arranged in parallel and a second limiting plate 211 located between the two second outer limiting walls 21, and the second limiting plate 211 is provided with a second protrusion 2111; and the fastener 4, including a third plug-in portion plugged in with the first plug-in portion, and a fourth plug-in portion plugged in with the second plug-in portion, where the third plug-in portion includes two first inner limiting walls 41 that have a T-shaped longitudinal section and that match the first outer limiting walls 11 (the first inner limiting wall 41 having a T-shaped longitudinal section includes two plate cuboid objects perpendicular to each other, of which an upper platy object is horizontally arranged, and a lower platy object is vertically arranged), and a third limiting plate arranged between the two first inner limiting walls 41 and matching the first limiting plate 111 (the third limiting plate is arranged in parallel with the upper platy object of the first inner limiting wall 41), where the third limiting plate is provided with a first groove 411 for mating with the first protrusion 1111; and the fourth plug-in portion includes two second inner limiting walls 42 that have a T-shaped longitudinal section and that match the second outer limiting walls 21 (the second inner limiting wall 42 having a T-shaped longitudinal section includes two plate cuboid objects perpendicular to each other, of which an upper platy object is horizontally arranged, and a lower platy object is vertically arranged), and a fourth limiting plate arranged between the second inner limiting walls 42 and matching the second limiting plate 211 (the fourth limiting plate is arranged in parallel with the upper platy object of the second inner limiting wall 42), where the fourth limiting plate is provided with a second groove 421 for mating with the second protrusion 2111. The inner needle assembly 1 and the fastener 4 are plugged in together through the first protrusion 1111 of the first plug-in portion and the first groove 411 of the third plug-in portion, and the outer needle assembly 2 and the fastener 4 are plugged in together through the second protrusion 2111 of the second plug-in portion and the second groove 421 of the fourth plug-in portion. With this connection method, assembly and disassembly operations are simple, and assembly and disassembly time is short, helping reduce preparation time and preparation work for medical staff in a surgery, thereby improving surgery efficiency.

The first outer limiting walls 11 are arranged perpendicular to the first limiting plate 111 (the first outer limiting wall 11 is parallel with the lower platy object of the first inner limiting wall 41, and the first limiting plate 111 is parallel with the third limiting plate), and a first gap 15 is provided between each of the first outer limiting walls 11 and the first limiting plate 111; two first sliding slots are symmetrically provided on a surface of the first limiting plate 111 facing away from the first protrusion 1111; the second outer limiting walls 21 are arranged perpendicular to the second limiting plate 211 (the second outer limiting wall 21 is parallel with the lower platy object of the second inner limiting wall 42, and the second limiting plate 211 is parallel with the fourth limiting plate), and a second gap 25 is provided between each of the second outer limiting walls 21 and the second limiting plate 211; and two second sliding slots are symmetrically provided on a surface of the second limiting plate 211 facing away from the second protrusion 2111.

A third gap is provided between each of the first inner limiting walls 41 and the third limiting plate. When the fastener 4 is connected to the inner needle assembly 1, the first inner limiting walls 41 are inserted into the first gaps 15, the first limiting plate 111 is inserted into the third gaps, the first sliding slots abut against the top of the first inner limiting walls 41 (the first sliding slot mates with the upper platy object of the first inner limiting wall 41, and the first sliding slot is located below the upper platy object of the first inner limiting wall 41), and the first limiting plate 111 abuts against the third limiting plate, so that the first protrusion 1111 mates with the first groove 411. When the fastener 4 needs to be separated from the inner needle assembly 1, the first protrusion 1111 is pulled out from the first groove 411 by pulling up the third plug-in portion, so that the first inner limiting walls 41 are pulled out from the first gaps 15, and the first limiting plate 111 is separated from the third limiting plate. With this connection method, assembly and disassembly are simple, and assembly and disassembly time is short.

A fourth gap is provided between each of the second inner limiting walls 42 and the third limiting plate. When the fastener 4 is connected to the outer needle assembly 2, the second inner limiting walls 42 are inserted into the second gaps 25, the second limiting plate 211 is inserted into the fourth gaps, the second sliding slots abut against the top of the second inner limiting walls 42, and the second limiting plate 211 abuts against the fourth limiting plate, so that the second protrusion 2111 mates with the second groove 421. When the fastener 4 needs to be separated from the outer needle assembly 2, the second protrusion 2111 is pulled out from the second groove 421 by pulling up the fourth plug-in portion, so that the second inner limiting walls 42 are pulled out from the second gap 25, and the second limiting plate 211 is separated from the fourth limiting plate. With this connection method, assembly and disassembly are simple, and assembly and disassembly time is short.

The inner needle assembly 1 is nested within the outer needle assembly 2, and the first plug-in portion protrudes from the outer needle assembly 2. The inner needle assembly 1 can move inside the outer needle assembly 2 during use.

The outer needle assembly 2 further includes a hollow second needle body 24 at one end of the second plug-in portion, the second needle body 24 has openings at both ends, and the end of the second needle body 24 is of a needle-like structure; the inner needle assembly 1 further includes a first needle body 14 at one end of the first plug-in portion, and the end of the first needle body 14 is of a needle-like structure disposed in a direction opposite the needle-like structure at the end of the second needle body 24; and an accommodating portion (not shown) is provided on the first needle body 14 at a location close to the end of the first needle body 14. When the biopsy needle is in use, the first needle body 14 moves out from the end of the second needle body 24, the end of the first needle body 14 is inserted into a to-be-sampled skin tissue, and the second needle body 24 moves quickly to cover the first needle body 14, so that a small piece of the skin tissue is cut off and stored in the accommodating portion.

The first plug-in portion further includes a first connection portion 13 connected to the first needle body 14, and a first hole 12; planes corresponding to the first limiting plate 111, the first connection portion 13, and the first hole 12 are perpendicular to each other, the first plug-in portion includes a cuboid-shaped first body, and the first limiting plate 111, the first connection portion 13, and the first hole 12 are located on three mutually perpendicular and adjacent planes of the first body; and the biopsy needle is connected to a biopsy gun 6 through the first hole 12, and the first plug-in portion is connected to the first needle body 14 through the first connection portion 13.

The second plug-in portion further includes a second connection portion 23 connected to the second needle body 24, and a second hole 22; planes corresponding to the second limiting plate 211, the second connection portion 23, and the second hole 22 are perpendicular to each other, the second plug-in portion includes a cuboid-shaped second body, and the second limiting plate 211, the second connection portion 23, and the second hole 22 are located on three mutually perpendicular and adjacent planes of the second body; and the biopsy needle is connected to the biopsy gun 6 through the second hole 22. The second plug-in portion further includes a third connection portion (not shown) on a same axis as the second connection portion 23, the third connection portion runs through the second plug-in portion 23 and the second needle body 24, and the first needle body 14 enters the second plug-in portion through the third connection portion, and then enters the second needle body 24. The second plug-in portion includes the cuboid-shaped second body, the second limiting plate 211, the second connection portion 23, and the second hole 22 are located on three mutually perpendicular and adjacent planes of the second body, the third connection portion, the second limiting plate 211, and the second hole 22 are located on three mutually perpendicular and adjacent planes of the second body, and a plane corresponding to the third connection portion is parallel to a plane corresponding to the second connection portion 23.

The second needle body 24 is further provided with a cylindrical protective cover 3 wrapping the second needle body 24. The protective cover 3 can protect the second needle body 24 against contamination, further preventing a surgery from being affected. Therefore, when the biopsy needle is not in use, the protective cover 3 is sleeved on the second needle body 24, and when the biopsy needle needs to be used, the protective cover 3 can be removed directly.

The third plug-in portion and the fourth plug-in portion are on a same side of the fastener 4 and arranged in parallel.

The fastener 4 further includes a pull portion 43 and a through hole 44 on one side of the pull portion 43. When the fastener 4 needs to be separated from the inner needle assembly 1 and the outer needle assembly 2, an operator grasps the pull portion 43 and the through hole 44 to remove the fastener 4 from the inner needle assembly 1 and the outer needle assembly 2. The through hole 44 can be used as a force exertion point. Through the through hole 44, the operator can easily remove the fastener 4 from the inner needle assembly 1 and the outer needle assembly 2.

Figure 6:
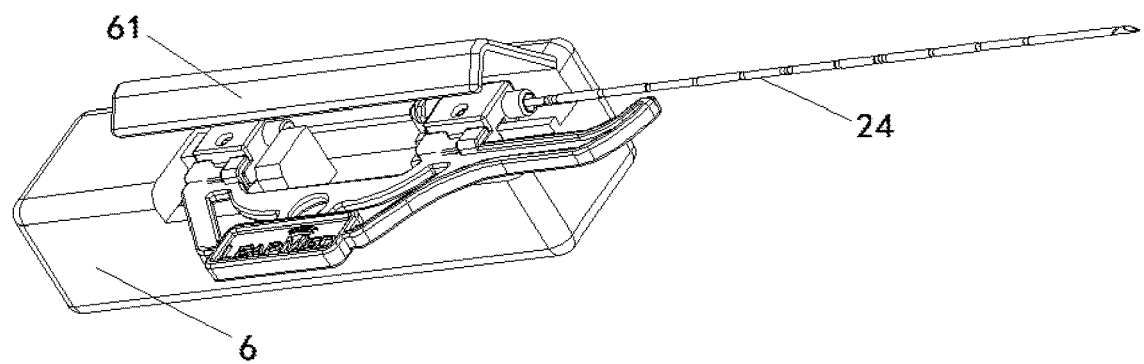
FIG. 6 is a schematic structural diagram of a puncture biopsy apparatus according to an embodiment of the present invention.

As shown in FIG. 6, a puncture biopsy apparatus according to the present invention includes a biopsy gun and a biopsy needle. When in use, a cover 61 of the biopsy gun 6 is opened, then the biopsy needle is fastened on the biopsy gun 6 through a first hole 12 and a second hole 22, and then a fastener 4 is removed from the biopsy needle by separate the fastener 4 from an inner needle assembly 1 and an outer needle assembly 2. Specifically, an operator holds a pull portion 43, then pulls the pull portion 43 outward or upward, and then closes the cover 61 after the fastener 4 is removed to complete the installation of the biopsy gun 6. Therefore, the biopsy needle can be assembled and disassembled in a simple and fast way, helping reduce preparation time and work for a surgery, and improving work efficiency of medical staff. In addition, the biopsy needle in the present invention has a simple structure and therefore can reduce mold costs for the biopsy needle and time for an employee to assemble the biopsy needle, thereby reducing production costs for a company.

The foregoing embodiments do not constitute any limitation on the protection scope of the present invention. A person skilled in the art should understand that, various modifications, combinations, sub-combinations, and substitutions may be made depending on a design requirement and other factors. Any modification, equivalent replacement, and improvement made without departing from the spirit and principle of the present invention shall fall within the protection scope of the present invention.

The invention claimed is:

1. A biopsy needle, comprising:
   an inner needle assembly, comprising a first plug-in portion plugged in with a fastener, wherein the first plug-in portion comprises two first outer limiting walls arranged in parallel and a first limiting plate located between the two first outer limiting walls, and the first limiting plate is provided with a first protrusion;
   an outer needle assembly, comprising a second plug-in portion plugged in with the fastener, wherein the second plug-in portion comprises two second outer limiting walls arranged in parallel and a second limiting plate located between the two second outer limiting walls, and the second limiting plate is provided with a second protrusion; and
   the fastener, comprising a third plug-in portion plugged in with the first plug-in portion, and a fourth plug-in portion plugged in with the second plug-in portion, wherein the third plug-in portion comprises two first inner limiting walls that have a T-shaped longitudinal section and that align with the first outer limiting walls, and a third limiting plate arranged between the two first inner limiting walls and aligning with the first limiting plate, wherein the third limiting plate is provided with a first groove mating with the first protrusion; and the fourth plug-in portion comprises two second inner limiting walls that have a T-shaped longitudinal section and that align with the second outer limiting walls, and a fourth limiting plate arranged between the second inner limiting walls and aligning with the second limiting plate, wherein the fourth limiting plate is provided with a second groove mating with the second protrusion.

2. The biopsy needle according to claim 1, wherein the first outer limiting walls are arranged perpendicular to the first limiting plate, and a first gap is provided between each of the first outer limiting walls and the first limiting plate; two first sliding slots are symmetrically provided on a surface of the first limiting plate facing away from the first protrusion; the second outer limiting walls are arranged perpendicular to the second limiting plate, and a second gap is provided between each of the second outer limiting walls and the second limiting plate; and two second sliding slots are symmetrically provided on a surface of the second limiting plate facing away from the second protrusion.

3. The biopsy needle according to claim 2, wherein a third gap is provided between each of the first inner limiting walls and the third limiting plate; and when the fastener is connected to the inner needle assembly, the first inner limiting walls are inserted into the first gaps, the first limiting plate is inserted into the third gaps, the first sliding slots abut against the top of the first inner limiting walls, and the first limiting plate abuts against the third limiting plate, so that the first protrusion mates with the first groove.

4. The biopsy needle according to claim 3, wherein a fourth gap is provided between each of the second inner limiting walls and the third limiting plate; and when the fastener is connected to the outer needle assembly, the second inner limiting walls are inserted into the second gaps, the second limiting plate is inserted into the fourth gaps, the second sliding slots abut against the top of the second inner limiting walls, and the second limiting plate abuts against the fourth limiting plate, so that the second protrusion mates with the second groove.

5. The biopsy needle according to claim 4, wherein the inner needle assembly is nested within the outer needle assembly, and the first plug-in portion protrudes from the outer needle assembly; the outer needle assembly further comprises a hollow second needle body at one end of the second plug-in portion; the inner needle assembly further comprises a first needle body at one end of the first plug-in portion; the first plug-in portion further comprises a first connection portion connected to the first needle body, and a first hole; planes corresponding to the first limiting plate, the first connection portion, and the first hole are perpendicular to each other; and the biopsy needle is connected to a biopsy gun through the first hole.

6. The biopsy needle according to claim 5, wherein the second plug-in portion further comprises a second connection portion connected to the second needle body, and a second hole, and planes corresponding to the second limiting plate, the second connection portion, and the second hole are perpendicular to each other; and the biopsy needle is connected to the biopsy gun through the second hole.

7. The biopsy needle according to claim 1, wherein the third plug-in portion and the fourth plug-in portion are on a same side of the fastener and arranged in parallel.

8. The biopsy needle according to claim 1, wherein the fastener further comprises a pull portion and a through hole on one side of the pull portion.

9. A puncture biopsy apparatus, comprising a biopsy gun and a biopsy needle, the biopsy needle comprising:
   an inner needle assembly, comprising a first plug-in portion plugged in with a fastener, wherein the first plug-in portion comprises two first outer limiting walls arranged in parallel and a first limiting plate located between the two first outer limiting walls, and the first limiting plate is provided with a first protrusion;
   an outer needle assembly, comprising a second plug-in portion plugged in with the fastener, wherein the second plug-in portion comprises two second outer limiting walls arranged in parallel and a second limiting plate located between the two second outer limiting walls, and the second limiting plate is provided with a second protrusion; and the fastener, comprising a third plug-in portion plugged in with the first plug-in portion, and a fourth plug-in portion plugged in with the second plug-in portion, wherein the third plug-in portion comprises two first inner limiting walls that have a T-shaped longitudinal section and that align with the first outer limiting walls, and a third limiting plate arranged between the two first inner limiting walls and aligning with the first limiting plate, wherein the third limiting plate is provided with a first groove mating with the first protrusion; and the fourth plug-in portion comprises two second inner limiting walls that have a T-shaped longitudinal section and that align with the second outer limiting walls, and a fourth limiting plate arranged between the second inner limiting walls and aligning with the second limiting plate, wherein the fourth limiting plate is provided with a second groove mating with the second protrusion.

10. The puncture biopsy apparatus of claim 9, wherein the first outer limiting walls of the biopsy needle are arranged perpendicular to the first limiting plate, and a first gap is provided between each of the first outer limiting walls and the first limiting plate; two first sliding slots are symmetrically provided on a surface of the first limiting plate facing away from the first protrusion; the second outer limiting walls are arranged perpendicular to the second limiting plate, and a second gap is provided between each of the second outer limiting walls and the second limiting plate; and two second sliding slots are symmetrically provided on a surface of the second limiting plate facing away from the second protrusion.

11. The puncture biopsy apparatus of claim 10, wherein a third gap is provided between each of the first inner limiting walls and the third limiting plate; and when the fastener is connected to the inner needle assembly, the first inner limiting walls are inserted into the first gaps, the first limiting plate is inserted into the third gaps, the first sliding slots abut against the top of the first inner limiting walls, and the first limiting plate abuts against the third limiting plate, so that the first protrusion mates with the first groove.

12. The puncture biopsy apparatus of claim 11, wherein a fourth gap is provided between each of the second inner limiting walls and the third limiting plate; and when the fastener is connected to the outer needle assembly, the second inner limiting walls are inserted into the second gaps, the second limiting plate is inserted into the fourth gaps, the second sliding slots abut against the top of the second inner limiting walls, and the second limiting plate abuts against the fourth limiting plate, so that the second protrusion mates with the second groove.

13. The puncture biopsy apparatus of claim 12, wherein the inner needle assembly is nested within the outer needle assembly, and the first plug-in portion protrudes from the outer needle assembly; the outer needle assembly further comprises a hollow second needle body at one end of the second plug-in portion; the inner needle assembly further comprises a first needle body at one end of the first plug-in portion; the first plug-in portion further comprises a first connection portion connected to the first needle body, and a first hole; planes corresponding to the first limiting plate, the first connection portion, and the first hole are perpendicular to each other; and the biopsy needle is connected to the biopsy gun through the first hole.

14. The puncture biopsy apparatus of claim 13, wherein the second plug-in portion further comprises a second connection portion connected to the second needle body, and a second hole, and planes corresponding to the second limiting plate, the second connection portion, and the second hole are perpendicular to each other; and the biopsy needle is connected to the biopsy gun through the second hole.

15. The puncture biopsy apparatus of claim 9, wherein the third plug-in portion of the biopsy needle and the fourth plug-in portion of the biopsy needle are on a same side of the fastener and arranged in parallel.

16. The puncture biopsy apparatus of claim 9, wherein the fastener further comprises a pull portion and a through hole on one side of the pull portion.

* * * * *